(12) United States Patent
Galluzzo et al.

(10) Patent No.: US 12,369,884 B2
(45) Date of Patent: Jul. 29, 2025

(54) ENDOLUMINAL SHAFTS INCLUDING ULTRASOUND COUPLING CAPABILITY

(71) Applicant: Covidien LP, Mansfield, MA (US)

(72) Inventors: Paul M. Galluzzo, Godmanchester (GB); Rita Stella, Sandy (GB); Neil Pollock, Wimpole (GB)

(73) Assignee: Covidien LP, Mansfield, MA (US)

( * ) Notice: Subject to any disclaimer, the term of this patent is extended or adjusted under 35 U.S.C. 154(b) by 147 days.

(21) Appl. No.: 17/665,446

(22) Filed: Feb. 4, 2022

(65) Prior Publication Data

US 2022/0280134 A1 Sep. 8, 2022

Related U.S. Application Data

(60) Provisional application No. 63/156,891, filed on Mar. 4, 2021.

(51) Int. Cl.
*A61B 8/00* (2006.01)
*A61B 8/12* (2006.01)

(52) U.S. Cl.
CPC ............... *A61B 8/12* (2013.01); *A61B 8/445* (2013.01)

(58) Field of Classification Search
CPC .................................. A61B 8/12; A61B 8/445
See application file for complete search history.

(56) References Cited

U.S. PATENT DOCUMENTS

| | | | |
|---|---|---|---|
| 5,390,678 A | 2/1995 | Gesswein et al. | |
| 6,226,543 B1 | 5/2001 | Gilboa et al. | |
| 6,461,304 B1 * | 10/2002 | Tanaka | A61B 8/4488 600/462 |
| 6,461,314 B1 * | 10/2002 | Pant | A61B 8/445 601/2 |
| 6,711,429 B1 | 3/2004 | Gilboa et al. | |
| 7,604,601 B2 | 10/2009 | Altmann et al. | |
| 7,713,210 B2 | 5/2010 | Byrd et al. | |
| 8,323,202 B2 | 12/2012 | Roschak et al. | |
| 8,388,541 B2 | 3/2013 | Messerly et al. | |
| 8,428,691 B2 | 4/2013 | Byrd et al. | |
| 8,611,983 B2 | 12/2013 | Glossop | |
| 8,781,555 B2 | 7/2014 | Burnside et al. | |
| 8,849,382 B2 | 9/2014 | Cox et al. | |
| 9,259,269 B2 | 2/2016 | Ladtkow et al. | |
| 9,549,685 B2 | 1/2017 | Cox et al. | |
| 9,636,031 B2 | 5/2017 | Cox | |
| 9,649,048 B2 | 5/2017 | Cox et al. | |
| 9,668,809 B2 | 6/2017 | Mayse et al. | |
| 9,681,823 B2 | 6/2017 | Messerly et al. | |
| 9,993,295 B2 | 6/2018 | Ladtkow et al. | |
| 9,999,371 B2 | 6/2018 | Messerly et al. | |
| 10,165,962 B2 | 1/2019 | Messerly et al. | |
| 10,447,947 B2 | 10/2019 | Liu | |
| 10,639,004 B2 | 5/2020 | Byrd et al. | |
| 10,842,560 B2 | 11/2020 | Panescu et al. | |
| 10,849,695 B2 | 12/2020 | Cox et al. | |
| 11,134,915 B2 | 10/2021 | Burnside et al. | |
| 2016/0374710 A1 * | 12/2016 | Sinelnikov | A61B 17/3207 600/439 |
| 2019/0282204 A1 * | 9/2019 | Sudol | A61B 8/0883 |

* cited by examiner

Primary Examiner — Amal Aly Farag
(74) Attorney, Agent, or Firm — Weber Rosselli & Cannon LLP

(57) ABSTRACT

The present disclosure describes endoluminal shafts including a tubular body, a finger extending therefrom and an ultrasound transducer, and navigation systems associated therewith.

18 Claims, 7 Drawing Sheets

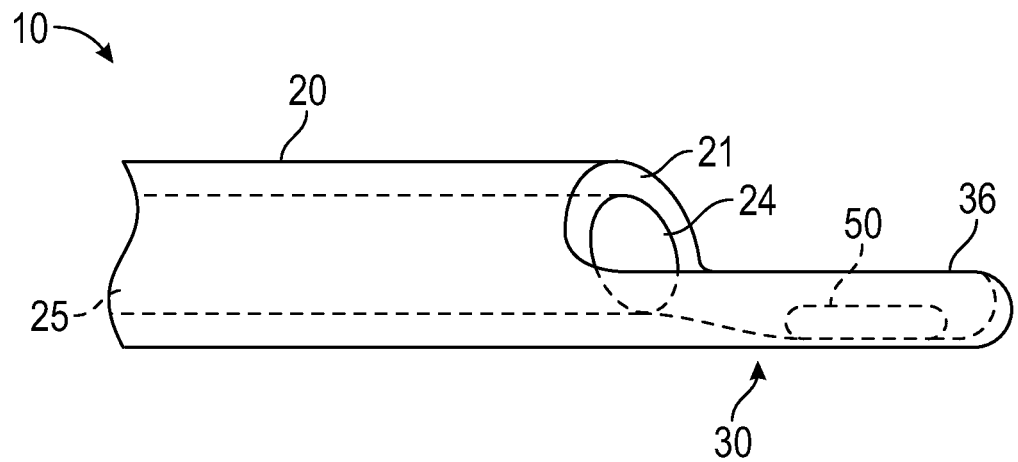
FIG. 3A
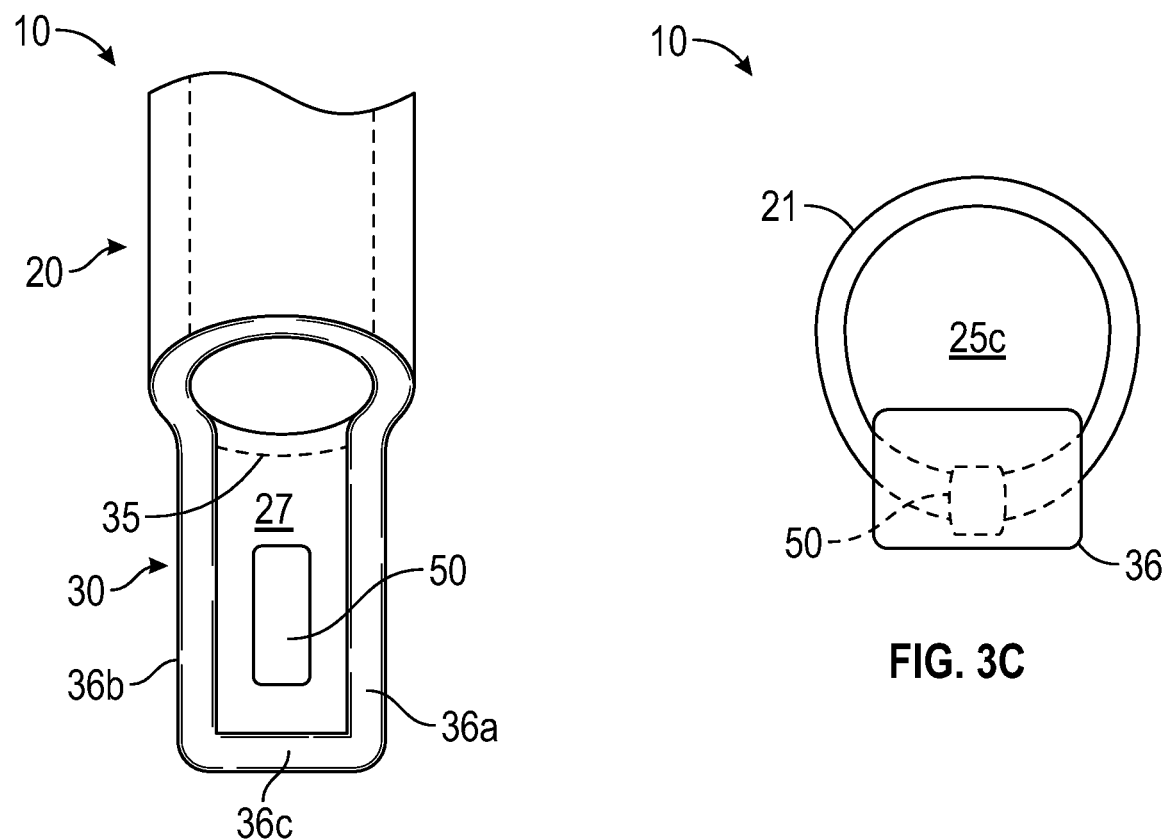
FIG. 3B
FIG. 3C

ENDOLUMINAL SHAFTS INCLUDING ULTRASOUND COUPLING CAPABILITY

CROSS-REFERENCE TO RELATED APPLICATIONS

This application claims benefit of and priority to U.S. Provisional Patent Application No. 63/156,891 filed Mar. 4, 2021, the disclosure of which is hereby incorporated by reference in its entirety.

BACKGROUND

Technical Field

The present technology is generally related to endoluminal shafts including ultrasound coupling capability, and more particularly, endoluminal shafts designed for navigation within a luminal body structure and including a tubular body, a finger extending therefrom, and an ultrasound transducer.

Description of Related Art

A wide variety of endoscopes and catheters, as well as surgical instruments designed to be used with such devices, have been developed. Of these known devices, each has certain advantages and disadvantages. However, there is an ongoing need to provide alternative endoscopes and/or catheters. For example, in some instances, some known endoluminal shafts may be unable to properly articulate inside a given tissue lumen and/or make solid contact with a given target tissue for proper ultrasound imaging. As one of ordinary skill would appreciate, ultrasound has difficulty imaging through air. Thus, there exists a need to provide at least portions of an endoluminal shaft with enhanced ultrasound coupling capabilities.

SUMMARY

The present disclosure describes an endoluminal shaft for navigation within a luminal structure, the shaft including ultrasound coupling capabilities. The endoluminal shaft has a tubular body including a sidewall defining a channel therein. The sidewall extending between a proximal end portion and a distal end portion of the tubular body. A finger extends distally or in a distal direction away from the distal end portion of tubular body. At least a portion of the finger may be flexible. The finger has a first side or first outer surface and a second side or second outer surface, the second side opposite the first side. The endoluminal shaft also includes an ultrasound transducer positioned on the first side of the finger.

In some embodiments, the tubular body of the endoluminal shaft further includes a distal port positioned on a distal end of the channel and/or proximal to the finger. The tubular body is configured to deliver at least one of an ultrasound-enhancing material, a second endoluminal shaft as described herein, or a surgical instrument, through the distal port and onto the finger including the ultrasound transducer.

In some embodiments, the finger of the endoluminal shaft is a generally planar body and/or arm that extends away from a bottom part of the distal end portion of the tubular body. In some embodiments, the first side of the finger aligns with a portion of an inner surface of the channel and the second side of the finger aligns with a portion of an outer surface of the tubular body.

In some embodiments, the finger of the endoluminal shaft is a curved bowl extending away from a bottom part of the distal end portion of the tubular body. In some instances, the ultrasound transducer is positioned within the curved bowl of the finger.

In some embodiments, the ultrasound transducer extends away vertically from the first side of the finger. In some embodiments, the ultrasound transducer is embedded at least partially in a thickness of the finger.

In some embodiments, the endoluminal shaft further includes a balloon positioned on a second side of the finger, opposite the ultrasound transducer positioned on the first side of finger. The balloon being configured to transition between a deflated configuration and an inflated configuration. The balloon further configured to cause the finger to pivot along a flexible portion of the finger. The flexible portion of the finger may be proximal to the balloon and/or the ultrasound transducer.

In some embodiments, the shaft may further include a stiffening member configured to transition between a locked position and an unlocked position. In the locked position the stiffening member prevents the flexible portion of the finger from pivoting. In the unlocked configuration, the stiffening member allows the flexible portion of the finger to pivot.

In some embodiments, the flexible portion may be configured to articulate. In such embodiments, the shaft may or may not include a balloon and/or a stiffening member.

In some embodiments, the endoluminal shafts described herein are configured to be used with electromagnetic navigation systems for navigating through a luminal network of a patient's lung. In some instances the system includes an endoscope or bronchoscope and a catheter, at least one which includes a finger extending distally therefrom and including an ultrasound transducer, and optionally a balloon. The systems may also include one or more of a computing device, a monitoring device, an electromagnetic board, and a tracking device.

BRIEF DESCRIPTION OF THE DRAWINGS

Various aspects and features of the present disclosure are described herein below with reference to the drawings, wherein:

FIG. 3A is a side view of an endoluminal shaft as described in at least one embodiment herein;

FIG. 3B is a top perspective view of the endoluminal shaft of FIG. 3A as described in at least one embodiment herein;

FIG. 3C is an end view of the endoluminal shaft of FIG. 3A as described in at least one embodiment herein;

DETAILED DESCRIPTION

The present disclosure describes an endoluminal shaft configured to navigate, treat and/or test within a luminal structure. The endoluminal shaft includes a tubular body, a finger extending therefrom, and an ultrasound transducer. The endoluminal shaft may be any endoscopic device suitable for insertion into a natural or artificial lumen defined within a patient. The endoluminal shaft may be configured to be used by a person or by a robotic surgical apparatus.

In some embodiments, the endoluminal shaft is an endoscope, including but not limited to, a sigmoidoscope, colonoscope, anoscope, laparoscope, or bronchoscope. In some embodiments, the endoluminal shaft is a catheter or extended working channel. In some embodiments, the endoluminal shaft is a surgical instrument, such as a locating guide, an imaging device, a guidewire, a surgical balloon, a biopsy tool, a cytology brush, an aspirating needle, or an ablation device.

In some embodiments, the endoluminal shaft is an endoscope, such as a bronchoscope, defining a channel configured to receive and/or maintain a catheter, extended working channel, and/or surgical instrument therein and/or therethrough.

In some embodiments, the endoluminal shaft is a catheter or extended working channel defining a channel configured to receive and/or maintain a surgical instrument therein and/or therethrough.

Figure 1A:
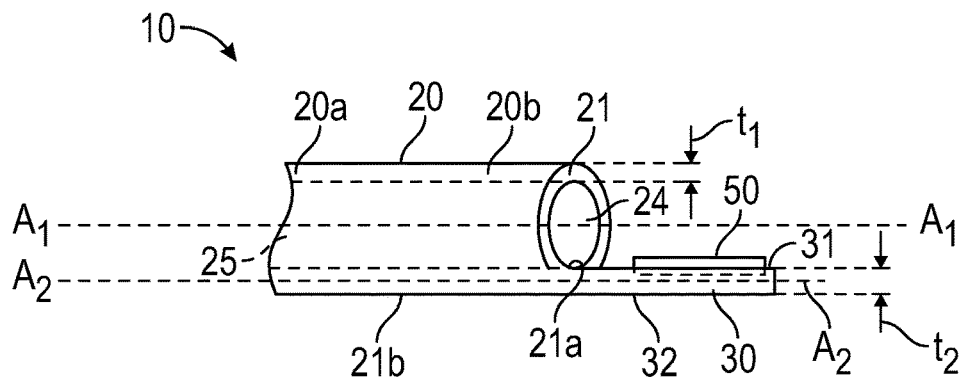
FIG. 1A is a side view of an endoluminal shaft as described in at least one embodiment herein.
Figure 1B:
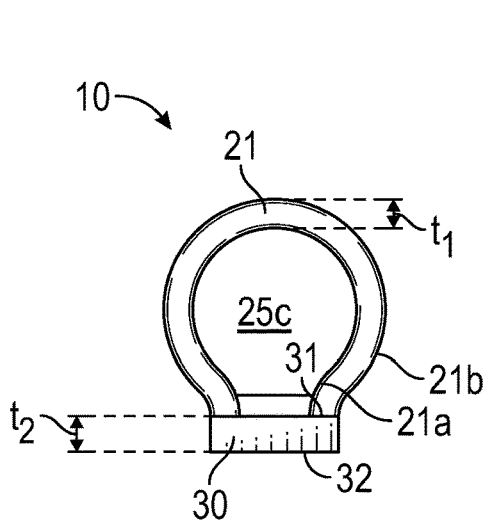
FIG. 1B is an end view of the endoluminal shaft of FIG. 1A as described in at least one embodiment herein
Figure 1C:
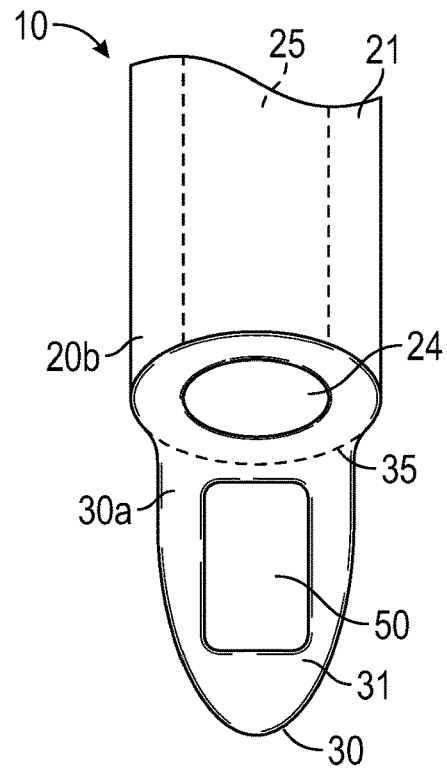
FIG. 1C is a top perspective view of the endoluminal shaft of FIG. 1A as described in at least one embodiment herein.

FIGS. 1A-1C depict an endoluminal shaft 10 as described herein. The shaft 10 includes a tubular body 20, a finger 30 extending distally from the tubular body 20, and an ultrasound transducer 50 positioned on the finger 30. The tubular body 20 has a sidewall 21 defining a channel 25 therein and/or therethrough. The tubular body 20 extends between a proximal end portion 20a and a distal end portion 20b. The sidewall 21 includes an inner surface 21a and an outer surface 21b opposite the inner surface 21a. The inner and outer surfaces 21a, 21b separated by a thickness of the sidewall $t_1$.

The tubular body 20 further includes a distal exit port 24 on a distal-most end 25c of the channel 25. The distal exit port 24 is proximal to the finger 30. The distal port 24 and the channel 25 may be configured to deliver an ultrasound-enhancing material therethrough to the finger 30 and/or the ultrasound transducer 50 positioned on the finger 30.

The ultrasound-enhancing material may be any suitable material configured to improve the ability of the ultrasound transducer 50 to make and/or maintain direct contact with the target, i.e., tissue or lesion, within the body of the patient. In some embodiments, the ultrasound-enhancing material is a gel material, such as a sterile, implantable, and/or bioabsorbable ultrasound gel.

As further depicted in FIGS. 1A-1C, the finger 30 is an extension of a bottom part of the distal end portion 20b of the tubular body 20. The finger 30 extends away in a distal direction from the distal end portion 20b of the tubular body 20, and particularly the distal-most end portion of the tubular body 20. The finger 30 includes a first side 31 and a second side 32 opposite the first side 31. The first and second sides 31, 32 are separated by a thickness $t_2$ of the finger 30.

In some embodiments, the thickness $t_1$ of the sidewall and the thickness $t_2$ of the finger are the same. In some embodiments, the thickness $t_1$ of the sidewall is greater than the thickness $t_2$ of the finger.

As further depicted in FIGS. 1A-1C, in some embodiments, the finger 30 is generally planar and defines a central longitudinal axis $A_2$ which is generally parallel to a central longitudinal axis of the tubular body $A_1$. In some embodiments, at least a portion, if not all, of the first side 31 of the finger 30 may be a continuation, i.e., longitudinally aligned with, of the inner surface 21a of the sidewall 21. In some embodiments, at least a portion, if not all, of the second side 32 of the finger 30 may be a continuation, i.e., longitudinally aligned with, of the outer surface 21b of the sidewall 21.

As depicted in FIG. 1C, the outer perimeter of the finger 30 may be generally free of sharp edges and/or rounded to assist the finger 30 in passing through a body lumen or tissue. In addition, in some embodiments, the finger is a flexible finger 30 including a flexible portion 35, and particularly a predetermined flex point 35 defined by a pleat or crease, in a proximal end portion 30a of the finger 30.

The one or more ultrasound transducers 50, as shown in FIGS. 1A-1C, is positioned on the first side 31 of the finger 30 and may be at least partially, if not completely, embedded within the thickness $t_2$ of the finger 30. Alternatively, in some embodiments, the transducer(s) may not be embedded within the finger and simply are positioned along the first side of the finger.

The one or more US transducers 50 are configured to transmit ultrasound waves and/or receive reflected ultrasound waves. Generally, the ultrasound waves penetrate the tissue surrounding the finger based on the frequency of the ultrasound waves. For example, 1 megahertz (MHz) ultrasound waves penetrate to a depth of 2 cm to 5 cm and 3 MHz ultrasound waves penetrate to a depth of 1.5 cm.

Generally, the US waves are reflected at a boundary where density changes or at the interface between tissues. During the navigation process, such as navigating the luminal network of the lung, the US waves are reflected from the inside wall of a bronchial tree, from the outside wall of the bronchial tree, and from a diseased portion or cancerous portion located at the outside wall of the bronchial tree and provide finite details of the lung structure and the tissue patency that could not otherwise be revealed using non-invasive imaging means. The reflected US waves have information such as amplitude and a delayed time between transmission of the US waves and reception of the reflected US waves. Since the US waves travels differently and attenuates amplitudes differently in accordance with the density of tissue, the amplitude and the delayed time may be used to identify a type of tissue, a density of the tissue, and/or a size of the tissue. Since the density of abnormal tissues (e.g., diseased, or cancerous cells) are different from the normal lung tissue, the reflected US waves may be used to identify the diseased or cancerous cells from normal cells and the size and/or thickness of the diseased or cancerous cells.

In addition, after the navigation process is complete, the US transducer can be used to identify at least one of the distal end portion of the catheter or the distal end portion of surgical instrument, extending through the distal exit port of the endoluminal shafts described herein.

Any suitable US transducer may be used. Some non-limiting examples include a radial transducer, a linear transducer, a piezoelectric transducer, and the like. In some embodiments, the US transducer is hard-wired with the wires extending along the sidewall of the tubular body. For example, the electrical wires for the US transducers may be positioned along either of the inner or outer surfaces of the sidewall, as is known in the art. In some embodiments, the electrical wires for the US transducers may be positioned within a lumen defined within the sidewall, as is known in the art. In some embodiments, the US transducers are wireless in construction and thus do not require any wires.

Figure 2:
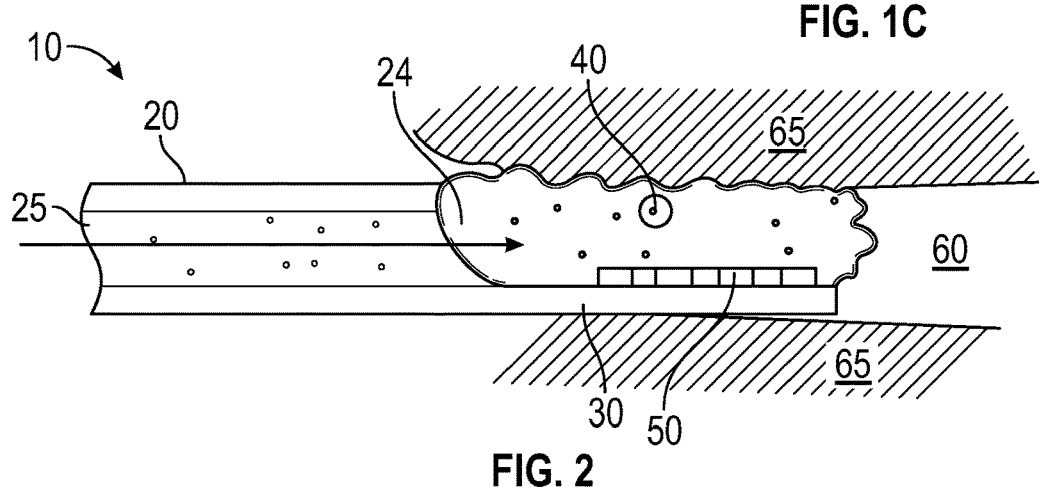
FIG. 2 is a schematic cross-sectional view of a portion of the endoluminal shaft of FIG. 1A positioned within a body lumen, as described in at least one embodiment herein.

Turning to FIG. 2, an endoluminal shaft 10 is shown positioned within a body lumen 60. As indicated by the arrow, the endoluminal shaft 10 is configured to deliver an ultrasound-enhancing material 40 through the channel 25 and the distal exit port 24 of the tubular body 20. The material 40 fills an air gap between the transducer 50 and the body tissue 65 defining the body lumen 60. The material 40 removes the air gap and couples the transducer 50 to the body tissue 65 for improved ultrasound imaging.

In FIGS. 3A-3C, the endoluminal shaft 10 may include a curved finger 30 defining a bowl 36 within which the US transducer 50 is positioned. The curved finger 30 and/or bowl 36 is configured to contain the ultrasound-enhancing material therein, over the transducer 50, after exiting the distal port 24. The bowl-shaped finger 36, unlike the planar version of FIG. 1A, directs the material over the transducer 50.

Figure 4A:
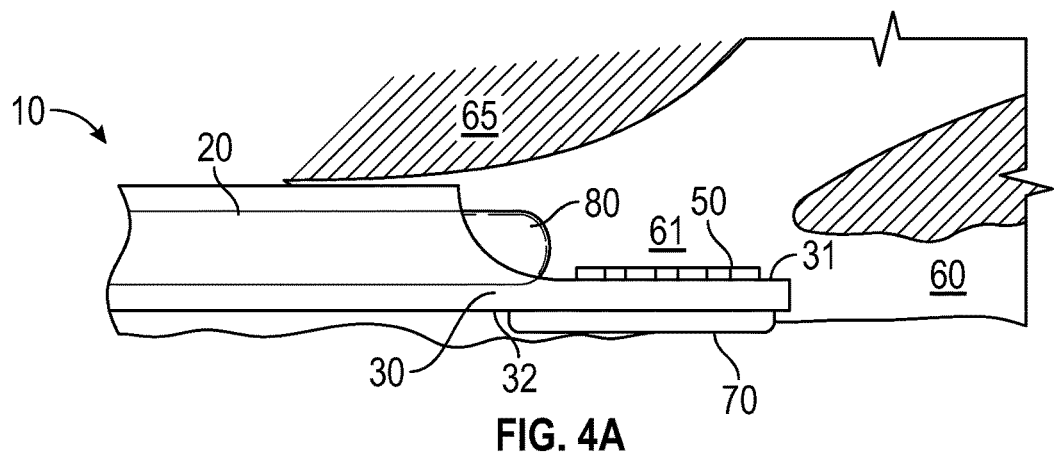
FIG. 4A is a schematic side view of a portion of an endoluminal shaft positioned within a body lumen, as described in at least one embodiment herein.
Figure 4B:
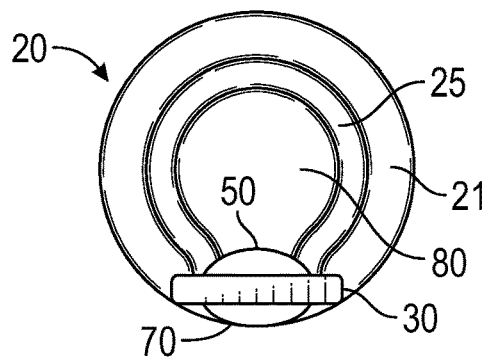
FIG. 4B is an end view of the endoluminal shaft of FIG. 4A as described in at least one embodiment herein.

In addition to the US transducer, the fingers described herein may further include a balloon. As shown in FIGS. 4A-4B, an endoluminal shaft 10 may include a finger 30 extending from a tubular body 20, the finger including an US transducer 50 on a first side 31 thereof and a balloon 70 on a second side 32 of the finger 30 opposite the transducer 50. The tubular body 20 including a sidewall 21 defining a channel 25 therein and/or therethrough. A distal exit port 24 positioned on the end of the channel 25 and proximal the finger 30. The balloon 70 in FIGS. 4A and 4B is depicted in a non-inflated state.

Figure 4C:
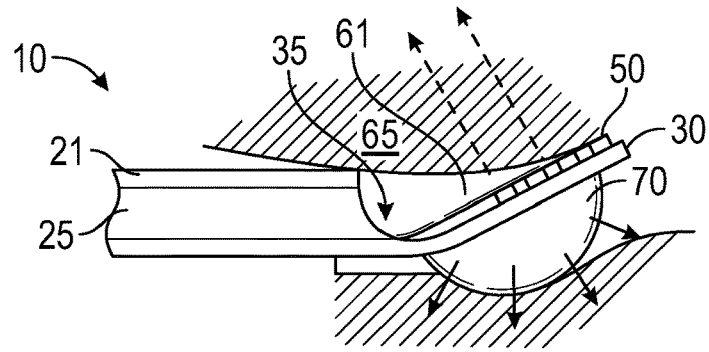
FIGS. 4C and 4D are schematic side views of the endoluminal shaft of FIG. 4A as described in at least one embodiment herein.

As illustrated in FIG. 4C, in some embodiments, the balloon 70 may be inflated as needed to cause the finger 30 to pivot via flexible portion 35 into direct contact with the tissue 65 of the body lumen 60. Although not depicted in FIG. 4C, the endoluminal shaft 10 may also be configured to deliver an ultrasound-enhancing material therethrough to fill any air gaps between the transducer 50 and the target tissue 65, before and/or after pivoting. As depicted, in some embodiments, the flexible finger 30 may include a single balloon 70, opposite the transducer 50, which defines a generally round or semi-circular outer shape when inflated. However, any number of balloons and any shape suitable for bending or flexing the finger relative to the shaft is envisioned.

As further depicted in FIG. 4C, in some embodiments, the balloon 70, at least in the non-inflated state, may extend along a greater length of the second side of the finger 30 than the length upon which the US transducer 50 extends along on the first side of the finger 30. It is envisioned that the increased length of the balloon 70, as compared to the length of the transducer 50, may enhance the likelihood of placing the entire surface area of the transducer 50 into direct with the tissue 65 and/or catheter or surgical instrument 80.

Figure 4D:
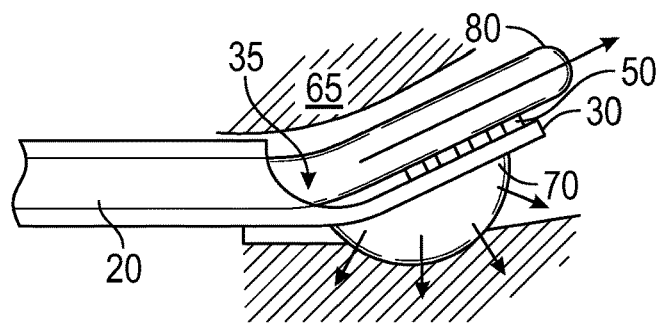

In FIG. 4D, in some embodiments, the balloon 70 may be inflated as needed to cause the finger 30 to pivot to steer a distal end of a catheter or surgical instrument 80 into a non-linear or bifurcated channel, as may be commonly found in bodily lumens such as lung tissue. Although not depicted in FIG. 4D, the endoluminal shaft 10 may also be configured to deliver an ultrasound-enhancing material therethrough to fill any gaps between the transducer 50 and the catheter or surgical instrument 80, as well as the target tissue 65.

As further depicted in FIGS. 4C-4D, in some embodiments, the balloon 70, at least in the non-inflated state, may be on opposite sides of the finger 30 and vertically off-set from the transducer 50. For example, as shown in FIGS. 4C and 4D, in some embodiments, the proximal end of the balloon 70 may be located closer to the distal end of the channel 25, the exit port 24, and/or the flexible portion 35, than the proximal end of the transducer 50. Since, in some instances, it can be more difficult to maneuver the proximal end of the transducer 50 (as opposed to the distal end of the transducer 50) into direct contact with the tissue 65, off-setting of the balloon 70 proximally from the transducer 50 may enhance the likelihood of placing the entire surface area of the transducer 50 into direct contact with the tissue 65 and/or catheter or surgical instrument 80.

Any suitable implantable balloon may be used. The balloon may be made from any elastic biocompatible material capable of transitioning between a non-expanded state and an expanded state. Some non-limiting examples include polymeric materials such as polyethylene terephthalate, polyolefins, and/or polyamide. The balloon may be made using any known suitable process, including but not limited to extrusion, molding, and the like.

In some embodiments, the shafts described herein may further include an inflation lumen extending a length of the shaft to the interior of the balloon. The inflation lumen configured to allow passage of any suitable liquid or gas therethrough, typically from outside the patient, to fill or empty the balloon in order to inflate or deflate, respectively, the balloon as needed. In some embodiments, as is known in the art, the inflation lumen may be positioned along or within the sidewalls of the shafts described herein. The inflation lumen continues along or within a portion of the finger to the balloon. A gas or liquid can be injected or removed from the balloon, via the lumen, to control the inflation or deflation of the balloon from outside the patient. In some embodiments, the liquid may be saline, water, or an ultrasound enhancing material such as ultrasound gels.

The endoluminal shafts described herein may be formed using any suitable method and/or any suitable biocompatible material known to those of ordinary skill. Some non-limiting examples of methods of forming the endoluminal shafts, include extrusion, molding, casting, pressing, and the like.

As shown in FIGS. 5A-5D, in some embodiments, an endoluminal shaft 10 as described herein may include a flexible finger 30 including a proximal flexible portion 35 extending along a first length ($l_1$) of the finger 30 and a distal non-flexible and/or stiff portion 37 extending along a second length ($l_2$) of the finger 30. In some embodiments, the second length ($l_2$) is greater than the first length ($l_1$). The transducer(s) 50 may be positioned on the first side 31 of the non-flexible portion 37. The balloon(s) 70 may be positioned on the second side 32 of the non-flexible portion 37.

Figure 5A:
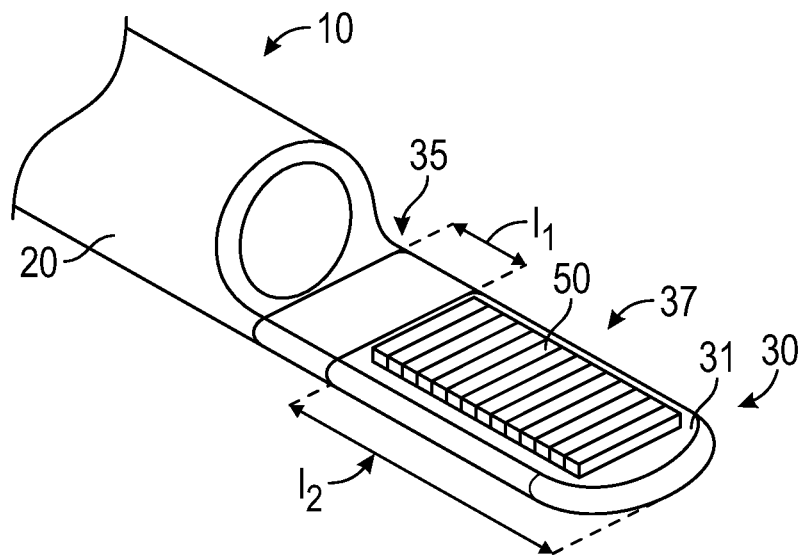
FIG. 5A is a perspective end view of an endoluminal shaft as described in at least one embodiment herein.
Figure 5B:
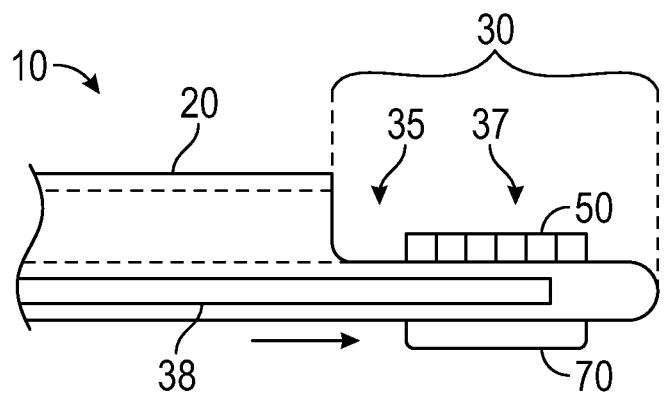
FIGS. 5B and 5C are a schematic cross-sectional view of one configuration of the endoluminal shaft of FIG. 5A as described in at least one embodiment herein.
Figure 5C:
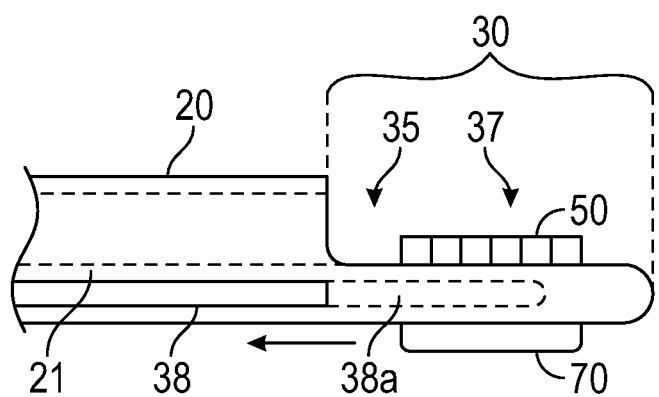

As specifically depicted in FIGS. 5B-5C, the shaft 10 may further include a stiffening member 38 configured to transition between a locked position (FIG. 5B) and an unlocked position (FIG. 5C). In some embodiments, the stiffening member 38 configured to slide longitudinally to transition between the locked and unlocked positions. In the locked position, the stiffening member 38 prevents the flexible portion 35 from pivoting. In such embodiments, the stiffening member 38 may extend along a length of at least a portion of the flexible portion 35, if not along the entire length of the flexible portion 35 and/or overlapping with at least a portion of the non-flexible portion 37. In the unlocked position, the stiffening member 38 allows the flexible portion 35 to pivot. In such embodiments, the stiffening member 38 may extend along a length of the tubular body 20 and not along a length of the flexible portion 35.

Figure 5D:
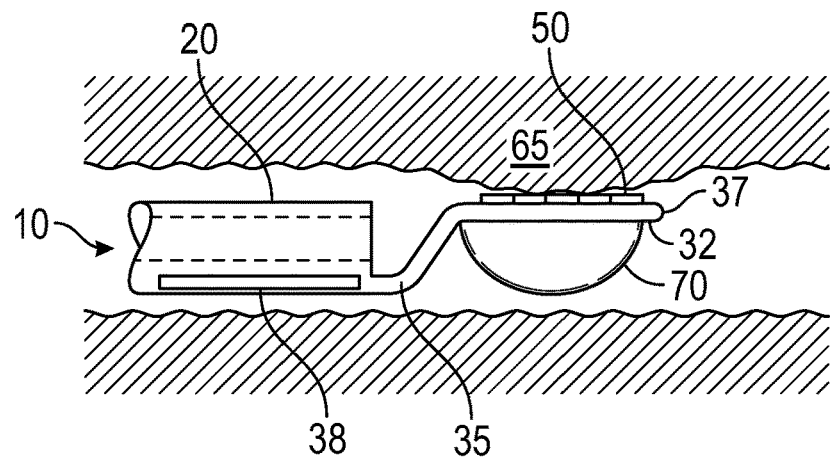
FIG. 5D is a schematic cross-sectional view of one configuration of the endoluminal shaft of FIG. 5A as described in at least one embodiment herein.

As shown in FIG. 5D, in some embodiments, in the unlocked position, the balloon 70 can be inflated to raise the non-flexible portion 37 (including the transducer 50) up against the tissue 65 while remaining generally longitudinal or parallel to the tissue 65. By remaining generally parallel to the tissue 65, more of the transducer 50 may be put into direct contact with the tissue 65 thereby improving US transmission therethrough.

As further shown in FIGS. 5B-5C, in some embodiments, the stiffening member 38 may be positioned within a member lumen 38a defined within the sidewall 21. However, it is envisioned that the stiffening member may alternatively by positioned along an exterior length of the outer surface of the tubular body (not shown).

The stiffening members described herein may be made of any biocompatible material have a stiffness greater than the flexible portion of the finger. The stiffening member may also include any suitable shape. In some embodiments, the stiffening member is a retractable rod. In some embodiments, the stiffening member is a retractable slat and/or rectangular-shaped piece.

Figure 6A:
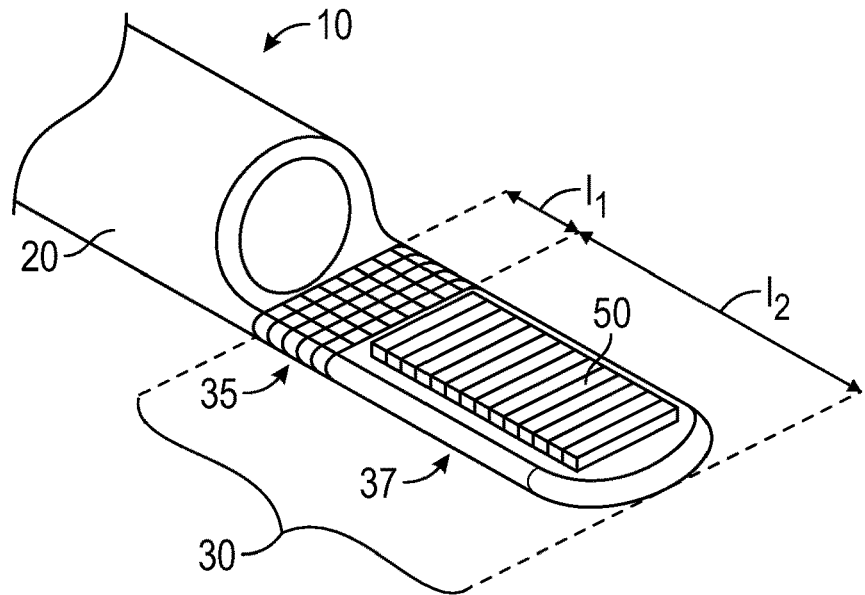
FIG. 6A is a perspective end view of an endoluminal shaft as described in at least one embodiment herein.
Figure 6B:
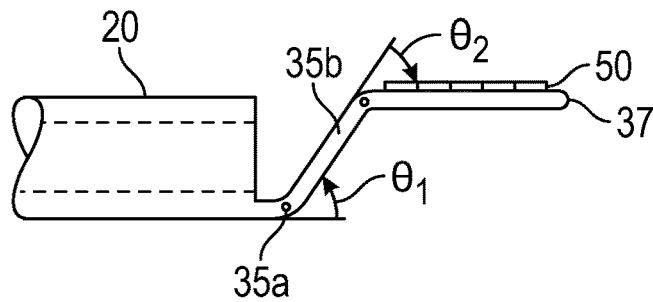
FIG. 6B is a schematic cross-sectional view of one configuration of the endoluminal shaft of FIG. 6A as described in at least one embodiment herein.

Turning to FIGS. 6A-6B, in some embodiments, an endoluminal shaft 10 as described herein may include a proximal flexible portion 35 extending along a first length ($l_1$) of the finger 30, wherein the flexible portion 35 may be configured to articulate. The actively articulatable flexible section 35 may pivot using any suitable articulation method including, but not intended to be limited to, the use of guidewires and/or concentric tubes.

As further shown in FIG. 6B, in some embodiments, each of the proximal and distal ends 35a, 35b of the articulatable flexible portion 35 may pivot causing the flexible portion 35 to transition between a first and second configuration. In the first configuration, the flexible portion 35 extends generally parallel to the longitudinal axis of the tubular body 20 and/or collinear to the non-flexible portion 37 of the finger 30 (FIG. 6A). In the second configuration, the flexible portion 35 extends at an angle transverse to the longitudinal axis of the tubular body 20 and/or non-collinear to the non-flexible portion 37. In some embodiments, as further shown in FIG. 6B, the second configuration forms a generally Z-shaped configuration. A balloon may or may not be included.

The various endoluminal shafts described herein are configured to be used with systems for visualizing a luminal network of a patient, and/or particularly a lung of a patient. The systems, endoscope assemblies, and/or catheter assemblies as described herein may use ultrasound (US) imaging technologies which provide a sufficient resolution to identify and locate a target for diagnostic, navigation, and treatment purposes. US imaging, particularly in conjunction with non-invasive imaging, can provide a greater resolution and enable luminal network mapping and target identification. Further, additional clarity is provided with respect to tissue adjacent the endoluminal shaft, and particularly the flexible finger extending from a distal end thereof, which can result in different treatment options being considered to avoid adversely affecting other adjacent tissue.

Figure 7:
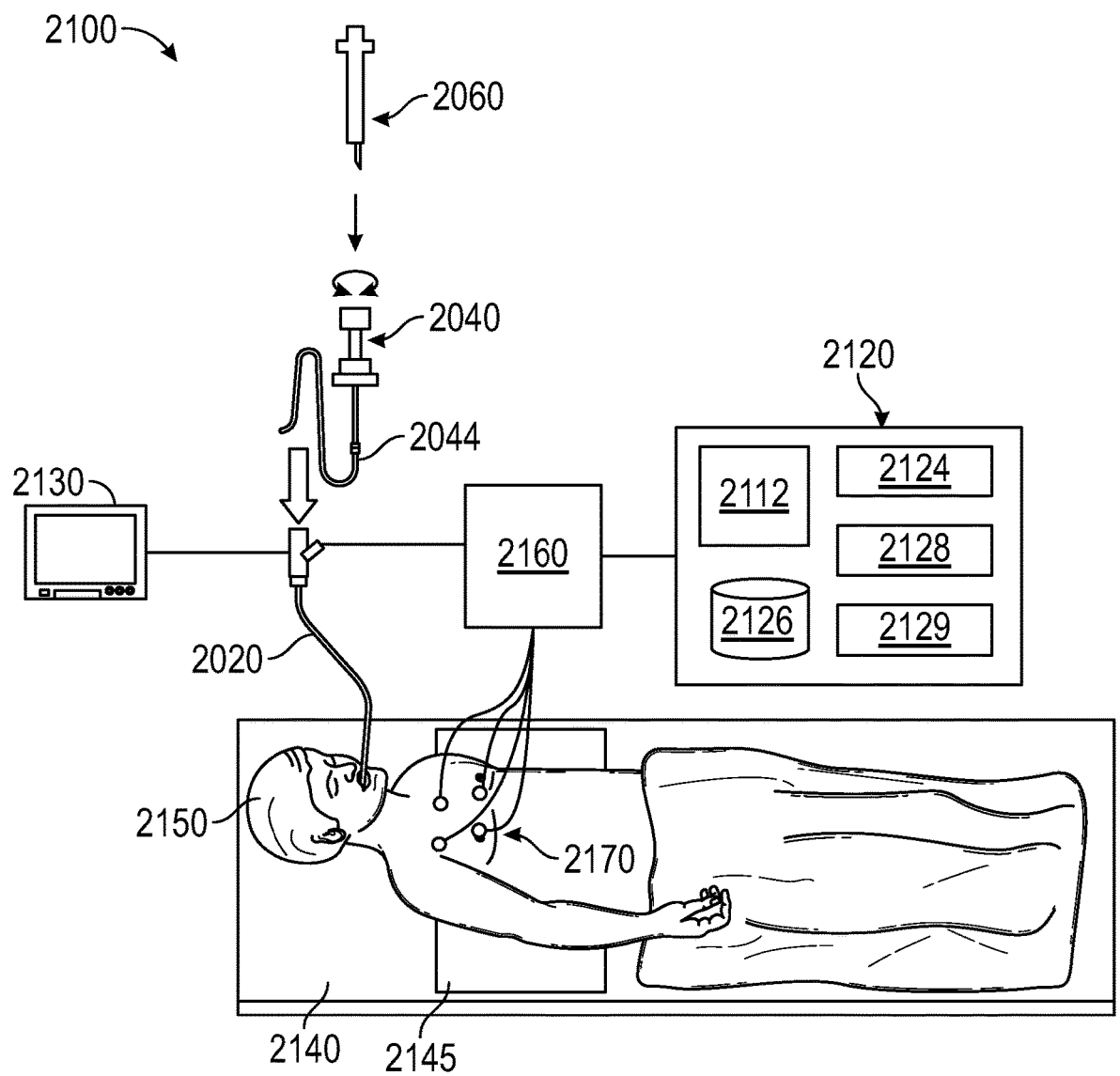
FIG. 7 is a schematic perspective view of a navigation system for visualizing a lung of a patient as described in at least one embodiment herein.

FIG. 7 illustrates an electromagnetic navigation (EMN) system 2100, which is configured to augment CT, MRI, or fluoroscopic images, with US image data assisting in navigation through a luminal network of a patient's lung to a target. One such EMN system may be the ELECTROMAGNETIC NAVIGATION BRONCHOSCOPY® system currently sold by Covidien LP. The system 2100 includes an endoscope 2020 and/or a catheter 2040, at least one of which includes an endoluminal shaft having a flexible finger as described herein extending from a distal end thereof. The system may further include a surgical instrument 2060, a computing device 2120, a monitoring device 2130, an EM board 2140, a tracking device 2160, and reference sensors 2170. The endoscope 2020 is specifically a bronchoscope which is operatively coupled to the computing device 2120 and the monitoring device 2130 via wired connection (as shown in FIG. 15 or wireless connection (not shown).

The bronchoscope 2020 is inserted into the mouth of the patient 2150 and captures images of the luminal network of the lung. In the EMN system 2100, inserted into the bronchoscope 2020 is a catheter 2040 for achieving access to the periphery of the luminal network of the patient 2150. The catheter 2040 may include an extended working channel (EWC) 2044 into which surgical instrument 2060 may be inserted. A first surgical instrument 2060, such as a locatable guide including an EM sensor at the distal tip thereof, may be inserted into the EWC 2044 to help navigate through the luminal network of the lung as described in greater detail below. Upon arrival of a desired location in the lung, the locatable guide may be removed from the EWC and replaced with a second surgical instrument configured to treat or biopsy a portion of the lung. As described herein, the endoscope or bronchoscope 2020 and/or the catheter 2040 may individually include a flexible finger as described herein extending from a distal end thereof.

The computing device 2120, such as, a laptop, desktop, tablet, or other similar computing device, includes a display 2122, one or more processors 2124, memory 2126, a network card 2128, and an input device 2129. The system 2100 may also include multiple computing devices, wherein the multiple computing devices 2120 are employed for planning, treatment, visualization, or helping clinicians in a manner suitable for medical operations. The display 2122 may be touch-sensitive and/or voice-activated, enabling the display 2122 to serve as both an input and output device. The display 2122 may display a two dimensional (2D) images or three dimensional (3D) model of a luminal network, such as found in the lung, to locate and identify a portion of the network that displays symptoms of disease, such as lung disease. The generation of such images and models is described in greater detail below. The display 2122 may further display options to select, add, and remove a target to be treated and settable items for the visualization of the network or lung. In an aspect, the display 2122 may also display the location of the catheter 2040 in the luminal network of the lung based on the 2D images or 3D model of the lung. For ease of description not intended to be limiting on the scope of this disclosure, a 3D model is described in detail below but one of skill in the art will recognize that similar features and tasks can be accomplished with 2D models and images.

The one or more processors 2124 execute computer-executable instructions. The processors 2124 may perform image-processing functions so that the 3D model of the lung can be displayed on the display 2122. In embodiments, the computing device 2120 may further include a separate graphic accelerator (not shown) that performs only the image-processing functions so that the one or more processors 2124 may be available for other programs.

The memory 2126 stores data and programs. For example, data may be image data for the 3D model or any other related data such as patients' medical records, prescriptions and/or history of the patient's diseases. One type of programs stored in the memory 2126 is a 3D model and pathway planning software module (planning software). An example of the 3D model generation and pathway planning software may be the ILOGIC® planning suite currently sold by Covidien LP. When image data of a patient, which is typically in digital imaging and communications in medicine (DICOM) format, from for example a CT image data set (or image data set by other imaging modality) is imported into the planning software, a 3D model of the bronchial tree is generated. In an aspect, imaging may be done by CT imaging, magnetic resonance imaging (MRI), functional MRI, X-ray, and/or any other imaging modalities. To generate the 3D model, the planning software employs segmentation, surface rendering, and/or volume rendering. The planning software then allows for the 3D model to be sliced or manipulated into a number of different views including axial, coronal, and sagittal views that are commonly used to review the original image data. These different views allow the user to review all of the image data and identify potential targets in the images.

Once a target is identified, the software enters into a pathway planning module. The pathway planning module develops a pathway plan to achieve access to the targets and the pathway plan pin-points the location and identifies the coordinates of the target such that they can be arrived at using the EMN system 2100 in combination with any of the endoluminal shafts described herein, and particularly the catheter 2040 together with the EWC 2044 and a surgical instrument 2060 such as the locatable guide 2060. The pathway planning module guides a clinician through a series of steps to develop a pathway plan for export and later use in during navigation to the target in the patient 2150. The term, clinician, may include doctor, surgeon, nurse, medical assistant, or any user of the pathway planning module involved in planning, performing, monitoring and/or supervising a medical procedure.

The memory 2126 may store navigation and procedure software which interfaces with the EMN system 2100 to provide guidance to the clinician and provide a representation of the planned pathway on the 3D model and 2D images derived from the 3D model. An example of such navigation software may be the ILOGIC® navigation and procedure suite sold by Covidien LP. In practice, the location of the patient 2150 in the EM field generated by the EM field generating device 2145 must be registered to the 3D model and the 2D images derived from the model. Such registration may be manual or automatic.

As further shown in FIG. 7, the EM board 2140 is configured to provide a flat surface for the patient to lie down and includes an EM field generating device 2145. When the patient 2150 lies down on the EM board 2140, the EM field generating device 2145 generates an EM field sufficient to surround a portion of the patient 2150. An EM sensor on a distal tip of the LG 2060 may be used to determine the location of the LG 2060 in the EM field generated by the EM field generating device 2145.

In some embodiments, the EM board 2140 may be configured to be operatively coupled with the reference sensors 2170 which are located on the chest of the patient 2170. The reference sensors 2170 move up and down following the chest while the patient 2150 is inhaling and move down following the chest while the patient 2150 is exhaling. The movement of the reference sensors 2170 in the EM field is captured by the reference sensors 2170 and transmitted to the tracking device 2160 so that the breathing pattern of the patient 2150 may be recognized. The tracking device 2160 also receives outputs of the EM sensor on the LG 2060, combines both outputs, and compensates the breathing pattern for the location of the LG 2060. In this way, the location identified may be compensated for so that the compensated location of the LG 2060 is synchronized with the 3D model of the lung. Once the patient 2150 is registered to the 3D model, the position of the EWC 2044 (of the endoscope or catheter assemblies described herein) and particularly the LG 2060 can be tracked within the EM field generated by the EM field generator 2145, and the position of the LG 2060 can be depicted in the 3D model or 2D images of the navigation and procedure software.

When the endoscope 2020 or catheter 2040, and the LG 2060, reaches a target tissue by following the pathway plan, the LG 2060 including the EM sensor confirms its location at the target and a clinician may confirm the location at the target. Once confirmed, the LG 2060 may be removed from the catheter 2040 and/or endoscope 2020. At this point, in some embodiments, an ultrasound enhancing material may be injected through the distal exit port of the catheter or endoscope covering the US transducer located on the flexible finger and indirectly connecting the US transducer to the target tissue (See, e.g., FIG. 2). Alternatively, or in combination with injecting the material, in some embodiments, a second surgical instrument 2060 such as biopsy tool or ablation catheter may be inserted into the EWC 2044 to the target to retrieve a sample of the target for confirmation of the disease or treat the target tissue. Further, in some embodiments, a balloon as described herein may be inflated to force the flexible finger to bend or flex out of plane relative to the endoluminal shaft of the endoscope or catheter in an effort to steer or direct the surgical instrument either towards the target tissue outside the body lumen or through a bifurcated body lumen. Any of the surgical instruments used to navigate, biopsy, or treat the target may be used. Any US transducers included with the flexible finger extending from a distal end portion of the endoluminal shafts described herein may then be used to transmit and receive US waves and the computing device 120 determines whether the flexible finger and/or treatment tool are properly situated relative to the distal end portion of the endoluminal shaft of the endoscope or catheter, as well as to the target tissue. By being properly aligned, the biopsy or treatment tool may perform with higher efficiency.

Figure 8A:
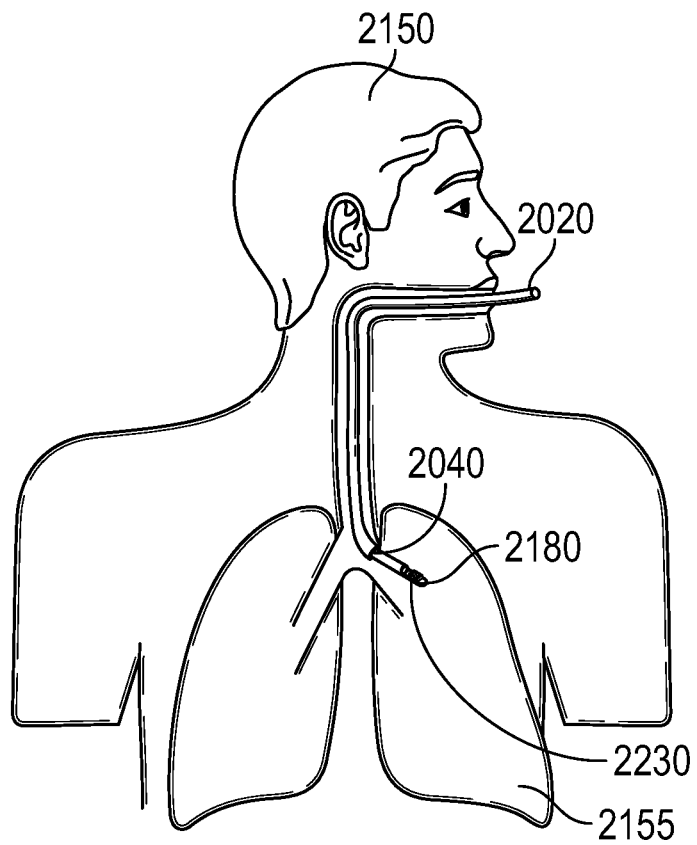
FIG. 8A is an illustration of an endoluminal shaft inserted into a lung as described in at least one embodiment herein.

FIG. 8A illustrates a bronchoscope 2020 and a catheter 2040 including a flexible finger 2230 as described herein inserted into the lungs 2155 via a natural orifice (e.g., the mouth) of a patient 2150 toward the target following a pathway plan. When the bronchoscope 2020 reaches a certain location of the lung 2155, the bronchoscope 2020 becomes wedged and cannot go further into bronchial tree due to the size constraints. Then, the catheter 2040 including an EWC may be used to navigate the luminal network to a target 2180 following the pathway plan, as described above. The EWC is small and thin enough to reach the target 2180.

Figure 8B:
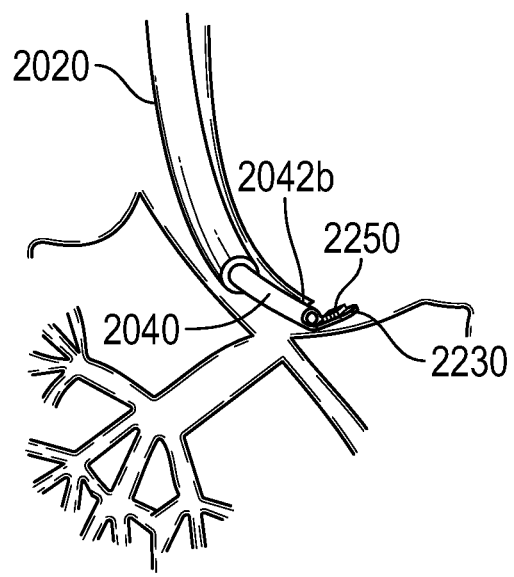
FIG. 8B is an enlarged detail view of the circled area of FIG. 8A.

FIG. 8B illustrates an enlarged detail view of the circled area of FIG. 8A, where the catheter 2040, and particularly the distal end portion 2042*b*, includes a flexible finger 2230 as described herein and including a US transducer 2250 on one side and optionally a balloon on a second side opposite the US transducer 2250. The flexible finger 2250 is shown bent or flexed out of plane relative to the distal end 2042*b* of the catheter 2040 to follow the bifurcated channel inside the lung. In this configuration, the analysis, treatment, or biopsy of the target tissue can be performed using US imaging to ensure proper placement of the shafts and/or any surgical instruments. Although not depicted, in some embodiments, an ultrasound enhancing material may also be injected through the catheter onto the US transducer of the flexible finger.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting but merely as exemplifications of particular embodiments. Those skilled in the art will envision other modifications within the scope and spirit of the claims appended hereto.

What is claimed is:

1. An endoluminal shaft for navigation within a luminal structure comprising:
    a tubular body including a sidewall defining a channel therein, the sidewall extending between a proximal end portion and a distal end portion of the tubular body, the sidewall on the distal end portion of the tubular body including an inner surface and an outer surface defining a thickness of the sidewall therebetween, the channel including an exit port positioned on a distal end of the tubular body, the exit port configured to deliver an ultrasound-enhancing material to body tissue;
    a finger including a first side and a second side opposite the first side defining a thickness of the finger therebetween, the finger being planar and extending distally from a bottom part of the distal end portion of the tubular body, wherein the exit port is proximal to the finger and the thickness of the finger is less than or equal to the thickness of the sidewall; and,
    an ultrasound transducer positioned on the first side of the finger.

2. The endoscope assembly of claim 1, wherein the tubular body is configured to deliver an ultrasound gel through the exit port to fill an air gap in the luminal structure between the transducer and body tissue.

3. The endoluminal shaft of claim 1, wherein the ultrasound transducer is embedded at least partially in a thickness of the finger.

4. The endoluminal shaft of claim 1, wherein the first side of the finger aligns with a portion of an inner surface of the channel and the second side of the finger aligns with a portion of an outer surface of the tubular body.

5. The endoluminal shaft of claim 1, wherein the finger is flexible.

6. The endoluminal shaft of claim 1, wherein the finger defines a central longitudinal axis which is parallel to a central longitudinal axis of the tubular body.

7. An endoluminal shaft for navigation within a luminal structure comprising:
    a tubular body including a sidewall defining a channel therein, the sidewall extending between a proximal end portion and a distal end portion of the tubular body, the sidewall on the distal end portion of the tubular body including an inner surface and an outer surface defining a thickness of the sidewall therebetween, the channel including an exit port positioned on a distal end of the tubular body, the exit port configured to deliver an ultrasound-enhancing material to body tissue;
    a flexible finger including a first side and a second side opposite the first side defining a thickness of the flexible finger therebetween, the flexible finger being planar and extending distally from a bottom part of the distal end portion of the tubular body, wherein the exit port is proximal to the flexible finger and the thickness of the flexible finger is less than or equal to the thickness of the sidewall;
    an ultrasound transducer positioned on the first side of the flexible finger; and,
    a balloon positioned on the second side of the flexible finger.

8. The endoscope assembly of claim 7, wherein the tubular body is configured to deliver a second endoluminal shaft through the exit port.

9. The endoluminal shaft of claim 7, wherein the ultrasound transducer extends from the first side of the flexible finger.

10. The endoluminal shaft of claim 7, wherein the ultrasound transducer is embedded at least partially in a thickness of the flexible finger.

11. The endoluminal shaft of claim 7, wherein the flexible finger further comprises balloon on the second side, the balloon configured to cause the flexible finger to pivot.

12. The endoluminal shaft of claim 7, wherein the flexible finger further comprises a proximal flexible portion extending along a first length of the flexible finger and a distal non-flexible portion extending along a second length of the flexible finger.

13. The endoluminal shaft of claim 12, further comprising a stiffening member configured to transition between a locked position and an unlocked position.

14. The endoluminal shaft of claim 12, wherein the proximal flexible portion of the flexible finger is configured to articulate.

15. An electromagnetic navigation system for navigating through a luminal network of a patient's lung, the system comprising:
    a computing device, a monitoring device,
    an electromagnetic board,
    a tracking device, and
    an endoluminal shaft including a tubular body including a sidewall defining a channel therein, the sidewall extending between a proximal end portion and a distal end portion of the tubular body, the sidewall on the distal end portion of the tubular body including an inner surface and an outer surface defining a thickness of the sidewall therebetween, the channel including an exit port positioned on a distal end of the tubular body, the exit port configured to deliver an ultrasound-enhancing material to body tissue, a flexible finger including a first side and a second side opposite the first side defining a thickness of the flexible finger therebetween, the flexible finger being planar and extending distally from a bottom part of the distal end portion of the tubular body, wherein the exit port is proximal to the flexible finger and the thickness of the flexible finger is less than or equal to the thickness of the sidewall, an ultrasound transducer positioned on the first side of the flexible finger, and optionally a balloon positioned on the second side of the flexible finger.

16. An endoluminal shaft for navigation within a luminal structure comprising:
 a tubular body including a sidewall extending between a proximal end portion and a distal end portion of the tubular body, the sidewall on the distal end portion of the tubular body including an inner surface and an outer surface defining a thickness of the sidewall therebetween, the inner surface of the sidewall defining a channel in the tubular body, the channel including an exit port positioned on a distal end of the tubular body, the exit port configured to deliver an ultrasound-enhancing material to body tissue;
 a finger which is an extension of the sidewall along a bottom part of the distal end portion of the tubular body and extending distally therefrom, the finger including a first outer side and a second outer side opposite the first outer side defining a thickness of the finger therebetween which is less than or equal to the thickness of the sidewall, wherein the exit port is proximal to the finger and the first outer side of the finger aligns with the inner surface of the sidewall along the bottom part of the distal end of the tubular body and the second outer side of the finger aligns with the outer surface of the sidewall along the bottom part of the distal end of the tubular body,
 an ultrasound transducer positioned on the first outer side of the finger.

17. The endoluminal shaft of claim 16, wherein the finger is a curved bowl and extends away from a bottom part of the distal end portion of the tubular body.

18. The endoluminal shaft of claim 17, wherein the ultrasound transducer is positioned within the curved bowl.

* * * * *